(12) United States Patent
Ohkubo

(10) Patent No.: US 10,059,648 B2
(45) Date of Patent: Aug. 28, 2018

(54) METHOD FOR PRODUCING FLUORINE-CONTAINING COMPOUNDS

(71) Applicant: DAIKIN INDUSTRIES, LTD., Osaka (JP)

(72) Inventor: Shun Ohkubo, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/576,398

(22) PCT Filed: May 18, 2016

(86) PCT No.: PCT/JP2016/064782
§ 371 (c)(1),
(2) Date: Nov. 22, 2017

(87) PCT Pub. No.: WO2016/194617
PCT Pub. Date: Dec. 8, 2016

(65) Prior Publication Data
US 2018/0155259 A1    Jun. 7, 2018

(30) Foreign Application Priority Data

May 29, 2015  (JP) ................................ 2015-110890

(51) Int. Cl.
| C07C 17/25 | (2006.01) |
| C07C 17/386 | (2006.01) |
| C07C 17/38 | (2006.01) |
| C07C 17/383 | (2006.01) |
| C07C 17/354 | (2006.01) |

(52) U.S. Cl.
CPC ............ *C07C 17/25* (2013.01); *C07C 17/354* (2013.01); *C07C 17/38* (2013.01); *C07C 17/383* (2013.01); *C07C 17/386* (2013.01)

(58) Field of Classification Search
CPC ........ C07C 17/25; C07C 17/386; C07C 17/38; C07C 17/354
See application file for complete search history.

(56) References Cited

U.S. PATENT DOCUMENTS 8,716,538 B2 *  5/2014  Merkel ................. C07C 17/087
570/155

FOREIGN PATENT DOCUMENTS

| JP | 2011-520856 | 7/2011 |
| JP | 2012-77086 | 4/2012 |
| JP | 2013-529640 | 7/2013 |
| JP | 2015-44843 | 3/2015 |
| WO | 2009/084703 | 7/2009 |
| WO | 2009/138764 | 11/2009 |
| WO | 2011/163285 | 12/2011 |
| WO | 2012/057367 | 5/2012 |

OTHER PUBLICATIONS

International Search Report dated Aug. 2, 2016 in International (PCT) Application No. PCT/JP2016/064782.

* cited by examiner

*Primary Examiner* — Jafar Parsa
(74) *Attorney, Agent, or Firm* — Wenderoth, Lind & Ponack, L.L.P.

(57) ABSTRACT

Provided is an efficient method for producing a fluorine-containing compound without the need for a rectification column involving numerous stages, extractive distillation, etc. The method for producing a fluorine-containing compound includes the step of supplying a composition containing a mixture to a dehydrohalogenation step, the mixture being at least one member selected from the group consisting of mixtures of at least one fluoroolefin and at least one hydrofluorocarbon, the boiling points of which are close to each other, azeotropic mixtures of at least one fluoroolefin and at least one hydrofluorocarbon, and pseudo-azeotropic compounds of at least one fluoroolefin and at least one hydrofluorocarbon.

24 Claims, No Drawings

METHOD FOR PRODUCING FLUORINE-CONTAINING COMPOUNDS

TECHNICAL FIELD

The present invention relates to a method for producing a fluorine-containing compound.

BACKGROUND ART

A fluorine-containing olefin represented by, for example, formula: $C_nF_mX_l$ wherein $m+l \leq 2n$ and $n \geq 2$, and Xs each independently represent F, Br, Cl, I, or H is a useful compound that has applications in various functional materials, solvents, refrigerants, foaming agents, etc., and is also useful as a monomer for functional polymers or as a starting material for a monomer. For example, a fluorine-containing olefin can be used as a monomer for modifying an ethylene-tetrafluoroethylene copolymer.

Fluorine-containing olefins have traditionally been produced by suitably combining a variety of reaction steps, such as fluorination, halogenation, defluorination, dehydrofluorination, dehalogenation, and dehydrohalogenation, using a variety of hydrocarbons and halogen-containing hydrocarbons as starting materials.

It is reported that 2,3,3,3-tetrafluoropropene (HFO-1234yf), which is seen as a promising low-global-warming-potential refrigerant compound, is produced by subjecting a chlorine-containing compound to a combination of reaction steps, such as fluorination, dehalogenation, and dehydrohalogenation (PTL 1). PTL 2 and 3 disclose a method for producing HFO-1234yf by repeating hydrogenation and dehydrofluorination using hexafluoropropene (HFP) as a starting material compound. Moreover, PTL 4 discloses a method for producing HFO-1234yf by catalytically dehydrogenating HFC-254eb and HFC-254fb.

For example, when HFP is used as a starting material compound, HFO-1234yf can be produced through the following reaction steps.

  (1)

  (2)

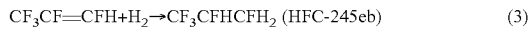  (3)

  (4)

CITATION LIST

Patent Literature

PTL 1: JP2015-44843A
PTL 2: JP2012-77086A
PTL 3: JP2011-520856A
PTL 4: JP2013-529640A

SUMMARY OF INVENTION

Technical Problem

The production method described above generates intermediates usable as starting materials for the target fluorine-containing olefin during the reaction steps, and supplying these intermediates to the reaction steps is preferable to obtain the target product. However, a useful intermediate may be in the form of a mixture containing an unnecessary by-product, and the intermediate and the by-product may have little difference in their boiling points, or they may form an azeotropic mixture or a pseudo-azeotropic mixture. These cases require a rectification column involving numerous stages and/or extractive distillation to separate the useful intermediate from the unnecessary by-product.

For example, the production of HFO-1234yf using HFP as a starting material compound as described above generates by-products, such as 1,3,3,3-tetrafluoropropene (HFO-1234ze), 1,1,1,2,2-pentafluoropropane (HFC-245cb), and 1,1,1,2,3-pentafluoropropane (HFC-245fa), in reaction step (4) to produce HFO-1234yf. Of these by-products, HFC-245cb can be a starting material for HFO-1234yf, and separating HFC-245cb from other by-products and subjecting it to dehydrofluorination is thus considered efficient. This process, however, requires a rectification column involving numerous stages and/or extractive distillation to separate HFC-245cb from HFO-1234ze due to the close boiling points of HFO-1234ze and HFC-245cb, and the need for such a rectification column and/or extractive distillation increases equipment costs and/or operation costs.

An object of the present invention is to provide such a method without the need for a rectification column involving numerous stages, extractive distillation, etc.

Solution to Problem

The present inventors conducted extensive research to achieve the object, and found that it is possible to efficiently produce a target fluorine-containing compound by supplying, to a dehydrofluorination step, at least part of a composition that contains at least one mixture selected from the group consisting of mixtures of at least one fluoroolefin and at least one fluorocarbon, the boiling points of which are close to each other, azeotropic mixtures of at least one fluoroolefin and at least one fluorocarbon, and pseudo-azeotropic compounds of at least one fluoroolefin and at least one fluorocarbon, without the need for a rectification column involving many stages or extractive distillation. The inventors conducted further research based on the findings and completed the invention. Specifically, the present invention relates to the following methods for producing a fluorine-containing compound.

Item 1.

A method for producing a fluorine-containing compound, the method comprising step D of supplying at least part of fluorine-containing compound-containing composition A to a dehydrohalogenation step, composition A containing a mixture that contains at least one fluoroolefin represented by formula (1):

  (1)

wherein n, m, and l represent an integer of 1 or more, $m+l=2n$, $n \geq 2$, and Xs each independently represent one atom selected from the group consisting of halogens and hydrogen, and at least one hydrofluorocarbon represented by formula (2):

  (2)

wherein p, q, r, and s represent an integer of 1 or more, $q+r+s=2p+2$, and Ys each independently represent one atom selected from the group consisting of halogens and hydrogen with at least one of Ys being a halogen atom, the difference in boiling point between the at least one fluoroolefin and the at least one hydrofluorocarbon being less than 9° C., or the at least one fluoroolefin and the at least one hydrofluorocarbon forming an azeotropic mixture or a pseudo-azeotropic mixture.

Item 2.

The production method according to Item 1 wherein the fluoroolefin represented by formula (1) is at least one halogenated fluoroolefin selected from the group consisting of 1,1,1,2,3-pentafluoropropene (HFO-1225ye), 1,1,1,3-tetrafluoropropene (HFO-1234ze), 1,1,1,3,3-pentafluoropropene (HFO-1225zc), 1,1,1-trifluoropropene (HFO-1243zf), 1,2-difluoroethylene (HFO-1132), 2,3,3,3-tetrafluoropropene (HFO-1234yf), hexafluoropropene (HFP), trifluoroethylene (HFO-1123), fluoroethylene (HFO-1141), tetrafluoroethylene (HFO-1114), and 1,1-difluoroethylene (HFO-1132a); and the hydrofluorocarbon represented by formula (2) is at least one saturated halogenated fluorocarbon selected from the group consisting of 1,1,1,2,2-pentafluoropropane (HFC-245cb), 1,1,1,3,3,3-hexafluoropropane (HFC-236fa), 1,1,1,2,3,3,3-heptafluoropropane (HFC-227ea), 1,1,2,2-hexafluoroethane (HFC-134), 1,1-difluoroethane (HFC-152a), 1,1,1,2-hexafluoroethane (HFC-134a), fluoroethane (HFC-161), 1,1,1-trifluoroethane (HFC-143a), and 1,1,1,2,2-pentafluoroethane (HFC-125).

Item 3.

The production method according to Item 1 or 2 wherein in step D the at least one hydrofluorocarbon represented by formula (2) is converted into at least one fluoroolefin represented by formula (3):

$$C_pF_qZ_t \qquad (3)$$

wherein p, q, and t represent an integer of 1 or more, p≥2, q+t=2p, and Zs each independently represent one atom selected from the group consisting of halogens and hydrogen to obtain fluorine-containing compound-containing composition B that contains a mixture that contains the at least one fluoroolefin represented by formula (1) and the at least one fluoroolefin represented by formula (3), the at least one fluoroolefin represented by formula (3) having a boiling point or boiling points that differ by 9° C. or more from that of the fluoroolefin represented by formula (1).

Item 4.

The production method according to Item 3 further comprising the step of separating at least part of fluorine-containing compound-containing composition B that contains a mixture that contains the at least one fluoroolefin represented by formula (1) and the at least one fluoroolefin represented by formula (3) into a fraction rich in the at least one fluoroolefin represented by formula (3) and a fraction containing a reduced amount of the at least one fluoroolefin represented by formula (3).

Item 5.

The production method according to Item 3 or 4 wherein the at least one fluoroolefin represented by formula (3) is at least one saturated halogenated fluorocarbon selected from the group consisting of 1,1,1,3,3-pentafluoropropene (HFO-1225zc), hexafluoropropene (HFP), trifluoroethylene (HFO-1123), fluoroethylene (HFO-1141), tetrafluoroethylene (HFO-1114), 1,1-difluoroethylene (HFO-1132a), and 2,3,3,3-tetrafluoropropene (HFO-1234yf).

Item 6.

The production method according to any one of Items 1 to 5 further comprising either a hydrogenation step or a fluorination step, or both of the steps.

Item 7.

The production method according to any one of Items 4 to 6 wherein the separation step comprises at least one member selected from the group consisting of distillation, extractive distillation, liquid-liquid separation, and membrane separation.

Item 8.

The production method according to any one of Items 1 to 7 wherein the fluorine-containing compound is at least one fluorine-containing compound selected from the group consisting of fluorine-containing compounds represented by formula (4):

$$CF_3CX=CYZ \qquad (4)$$

wherein X, Y, and Z each independently represent a fluorine atom or a hydrogen atom.

Item 9.

The production method according to Item 8 wherein the fluorine-containing compounds represented by formula (4) are at least one fluorine-containing compound selected from the group consisting of 1,1,1,3-tetrafluoropropene (HFO-1234ze) and 2,3,3,3-tetrafluoropropene (HFO-1234yf).

Item 10.

The production method according to any one of Items 1 to 9 wherein a starting material compound for producing the fluorine-containing compound contains at least one member selected from the group consisting of hexafluoropropene (HFP), 1,1,1,2,3-pentafluoropropene (HFO-1225ye), and 3-chloro-1,1,1,2,2-pentafluoropropane (HCFC-235cb).

Item 11.

The production method according to Item 10 wherein the fluorine-containing compounds represented by formula (4) are at least one fluorine-containing compound selected from the group consisting of 1,1,1,3-tetrafluoropropene (HFO-1234ze) and 2,3,3,3-tetrafluoropropene (HFO-1234yf), the starting material compound is at least one fluorine-containing compound selected from the group consisting of hexafluoropropene (HFP), 1,1,1,2,3-pentafluoropropene (HFO-1225ye), and 3-chloro-1,1,1,2,2-pentafluoropropane (HCFC-235cb), the at least one fluoroolefin represented by formula (1) is 1,1,1,3-tetrafluoropropene (HFO-1234ze), the at least one hydrofluorocarbon represented by formula (2) is 1,1,1,2,2-pentafluoropropane (HFC-245cb), and the at least one fluoroolefin represented by formula (3) is 2,3,3,3-tetrafluoropropene (HFO-1234yf).

Item 12.

The production method according to any one of Items 6 to 11 wherein at least one of the hydrogenation steps is a gas-phase reaction.

Item 13.

The production method according to any one of Items 6 to 11 wherein at least one of the hydrogenation steps is a liquid-phase reaction.

Item 14.

The production method according to any one of Items 6 to 13 wherein at least one of the fluorination steps is a gas-phase reaction.

Item 15.

The production method according to any one of Items 6 to 13 wherein at least one of the fluorination steps is a liquid-phase reaction.

Item 16.

A method for producing 2,3,3,3-tetrafluoropropene (HFO-1234yf), the method comprising the steps of 1) supplying at least 1,1,1,2,3-pentafluoropropene (HFO-1225ye) to a first hydrogenation step to obtain mixture product 1 containing 1,1,1,2,3-pentafluoropropane (HFC-245eb), 2) supplying mixture product 1 to a first dehydrohalogenation step to obtain mixture product 2 containing 2,3,3,3-tetrafluoropropene (HFO-1234yf) and 1,1,1,2,2-pentafluoropropane (HFC-245cb), 3) supplying mixture product 2 to a separation step to separate mixture product 2 into a mixture containing HFO-1234yf and a mixture containing HFO-1234ze and HFC-245cb, and 4) supplying the mixture containing HFO-1234ze and HFC-245cb to either the first dehydrohalogenation step or a dehydrohalogenation step other than the first dehydrohalogenation step, or both of the steps to dehydrohalogenate HFC-245cb, thereby converting HFC-245cb into HFO-1234yf.

Item 17.

The production method according to Item 16 wherein the mixture containing HFO-1234ze and HFC-245cb is supplied to a dehydrohalogenation step other than the first dehydrohalogenation step.

Item 18.

The production method according to Item 16 or 17 wherein a reaction temperature in the dehydrohalogenation step other than the first dehydrohalogenation step is higher than a reaction temperature in the first dehydrohalogenation step.

Item 19.

The production method according to any one of Items 16 to 18 comprising a separation step of recovering HFO-1234yf from the mixture obtained by subjecting the mixture containing HFO-1234ze and HFC-245cb to dehydrohalogenation.

Item 20.

A method for producing 2,3,3,3-tetrafluoropropene (HFO-1234yf), the method comprising the steps of 1) supplying at least hexafluoropropene (HFP) to a first hydrogenation step to obtain mixture product 1 containing 1,1,1,2,3,3-hexafluoropropane (HFC-236ea), 2) supplying mixture product 1 to a first dehydrohalogenation step to obtain mixture product 2 containing 1,1,1,2,3-pentafluoropropene (HFO-1225ye), 3) supplying mixture product 2 to a second hydrogenation step to obtain mixture product 3 containing HFC-245eb, 4) supplying mixture product 3 to a second dehydrohalogenation step to obtain mixture product 4 containing HFO-1234ze, HFC-245cb, and HFO-1234yf, and 5) supplying mixture product 4 to a separation step to separate mixture product 4 into a mixture containing HFO-1234yf and a mixture containing HFO-1234ze and HFC-245cb, and supplying the mixture containing HFO-1234ze and HFC-245cb to at least any one of the first dehydrohalogenation step and the second dehydrofluorination step, the first dehydrohalogenation step, the second dehydrohalogenation step, or a dehydrohalogenation step other than the first and second dehydrohalogenation steps to dehydrohalogenate HFC-245cb, thereby converting HFC-245cb into HFO-1234yf.

Item 21.

The production method according to Item 20 wherein the mixture containing HFO-1234ze and HFC-245cb is supplied to the first dehydrohalogenation step.

Item 22.

The production method according to Item 20 or 21 wherein mixture product 2 further contains HFO-1234ze, and mixture product 2 is supplied to the second hydrogenation step to convert HFO-1234ze into HFC-254fb.

Item 23.

The production method according to any one of Items 20 to 22 wherein a reaction temperature in at least one of the dehydrohalogenation steps to which the mixture containing HFO-1234ze and HFC-245cb is supplied is higher than a reaction temperature in the second dehydrohalogenation step.

Item 24.

The production method according to any one of Items 20 to 23 comprising a separation step of recovering HFO-1234yf from the mixture obtained by subjecting the mixture containing HFO-1234ze and HFC-245cb to dehydrohalogenation.

Advantageous Effects of Invention

The present invention provides a method for producing a target fluorine-containing compound at a lower equipment cost and/or operation cost by efficiently recovering at least one fluoroolefin from a composition that contains at least one mixture selected from the group consisting of mixtures of at least one fluoroolefin and at least one fluorocarbon, the boiling points of which are close to each other, azeotropic compositions of at least one fluoroolefin and at least one fluorocarbon, and pseudo-azeotropic compositions of at least one fluoroolefin and at least one fluorocarbon.

DESCRIPTION OF EMBODIMENTS

The following describes the present invention in detail.

Fluorine compounds are referred to by the names defined in the following table.

TABLE 1

| Name | Structural Formula | Name | Structural Formula |
|---|---|---|---|
| 1225ye | $CF_3CF=CHF$ | 245eb | $CF_3CHFCH_2F$ |
| 1234ze | $CF_3CH=CHF$ | 254fb | $CF_3CH_2CH_2F$ |
| 1225zc | $CF_3CH=CF_2$ | 245fa | $CF_3CH_2CHF_2$ |
| 1243zf | $CF_3CH=CH_2$ | 263fb | $CF_3CH_2CH_3$ |
| HFO-1132 | $CHF=CHF$ | HFC-152 | $CH_2FCH_2F$ |
| 1234yf | $CF_3CF=CH_2$ | 254eb | $CF_3CFHCH_3$ |
| HFP | $CF_3CF=CF_2$ | 236ea | $CF_3CFHCF_2H$ |
| HFO-1123 | $CH_2=CHF$ | HFC-161 | $CH_3CH_2F$ |
| HFO-1114 | $CF_2=CF_2$ | HFC-134 | $CHF_2CHF_2$ |
| 1132a | $CF_2=CH_2$ | 152a | $CHF_2CH_3$ |
| 245cb | $CF_3CF_2CH_3$ | FC-218 | $CF_3CF_2CF_3$ |
| 236fa | $CF_3CH2CF_3$ | HCFC-22 | $CHF_2Cl$ |
| 227ea | $CF_3CHFCF_3$ | HFC-143a | $CF_3CH_3$ |
| CF3I | $CF_3I$ | HFC-125 | $CF_3CHF_2$ |
| 134a | $CF_3CH_2F$ | HFC-32 | $CH_2F_2$ |
| c-C3F8 | $-CF_2CF_2CF_2-$ | | |

In this specification, if any of the fluorine-containing compounds shown in Table 1 has an isomer, the isomer is either E-isomer or Z-isomer, or both, unless otherwise specifically indicated.

Method for Producing Fluorine-Containing Compound

The method for producing a fluorine-containing compound according to the present invention comprises step D of supplying at least part of fluorine-containing compound-containing composition A to a dehydrohalogenation step, composition A containing a mixture that contains
at least one fluoroolefin represented by formula (1):

$$C_nF_mX_l \quad (1)$$

wherein n, m, and l represent an integer of 1 or more, m+l=2n, n≥2, and Xs each independently represent one atom selected from the group consisting of halogens and hydrogen with at least one of Xs being a halogen atom, and
at least one hydrofluorocarbon represented by formula (2):

$$C_pF_qY_rH_s \quad (2)$$

wherein p, q, r, and s represent an integer of 1 or more, q+r+s=2p+2, and Ys each independently represent one atom selected from the group consisting of halogens and hydrogen,
the difference in boiling point between the at least one fluoroolefin and the at least one hydrofluorocarbon being less than 9° C., or the at least one fluoroolefin and the at least one hydrofluorocarbon forming an azeotropic mixture or a pseudo-azeotropic mixture.

The dehydrohalogenation step can be performed in either a gas phase or a liquid phase.

In the dehydrohalogenation step, the reactor may further be supplied with a gas inert to the compound to be subjected to dehydrohalogenation and a catalyst, such as nitrogen, helium, and argon. However, mixing the compound to be subjected to dehydrohalogenation with an inert gas creates the need for separating the target product from the inert gas to recover the target product by, for example, rectification or extractive distillation. Because nitrogen, which is an inert gas, is a non-condensable gas, nitrogen and an organic component containing the target product are recovered together, and this may reduce the recovery rate of the target product. From this standpoint, when fluorine-containing compound-containing composition A is supplied to the reactor, the amount of the inert gas is preferably less than 50 mol %, more preferably less than 10 mol %, and particularly preferably less than 2 mol % of the total amount of fluorine-containing compound-containing composition A and the inert gas; and most preferably, inert gas is not present together with fluorine-containing compound-containing composition A.

In an embodiment of the present invention, step D may comprise the step of converting the hydrofluorocarbon represented by formula (2) into at least one fluoroolefin represented by formula (3): $C_pF_qZ_t$ wherein p, q, and t represent an integer of 1 or more, p≥2, q+t=2p, and Zs each independently represent one atom selected from the group consisting of halogens and hydrogen, the at least one fluoroolefin represented by formula (3) having a boiling point or boiling points different from that of the fluoroolefin represented by formula (1) by 9° C. or more, to thereby obtain easily purifiable fluorine-containing compound-containing composition B that contains a mixture of the at least one fluoroolefin represented by formula (1) and the at least one fluoroolefin represented by formula (3), the boiling points of these fluoroolefins being different by 9° C. or more.

In another embodiment of the present invention, step D may comprise the step of converting the hydrofluorocarbon represented by formula (2) into the at least one fluoroolefin represented by formula (3) that does not form an azeotropic mixture or a pseudo-azeotropic mixture with the fluoroolefin represented by formula (1) to thereby obtain easily purifiable fluorine-containing compound-containing composition B that contains a mixture of the at least one fluoroolefin represented by formula (1) and the at least one fluoroolefin represented by formula (3).

Because fluorine-containing compound-containing composition B contains at least one mixture selected from the group consisting of mixtures of fluoroolefins having different boiling points by 9° C. or more, non-azeotropic mixtures of fluoroolefins, and non-pseudo-azeotropic mixtures of fluoroolefins, part or all of the at least one fluoroolefin contained in fluorine-containing compound-containing composition B can be easily separated.

The step of separating part or all of the at least one fluoroolefin contained in fluorine-containing compound-containing composition B is not particularly limited, and the separation step may be, for example, at least one member selected from the group consisting of rectification, extractive distillation, liquid-liquid separation, and membrane separation.

The method for producing a fluorine-containing compound according to the present invention can further comprise either a hydrogenation step or a fluorination step, or both.

In the dehydrohalogenation step, a catalyst for typical dehydrohalogenation can be used. Examples of usable catalysts include halides and oxides of transition metal elements, Group 14 elements, and Group 15 elements. These catalysts have high affinity for a fluorine atom to be removed together with a metal element, and are thus considered to facilitate dehydrofluorination. Specific examples of transition metal elements include Ti, V, Cr, Mn, Fe, Co, Ni, Cu, Nb, and Ta. Specific examples of Group 14 elements include Sn and Pb. Specific examples of Group 15 elements include As, Sb, and Bi. Halides of these elements include fluorides and chlorides. Of these, SbCl5, SbCl3, SbF5, TaCl5, SnCl4, NbCl5, FeCl3, CrCl3, CrF3, TiCl4, MoCl5, Cr2O3, CoCl2, NiCl2, and the like are preferably used. These catalysts may be used singly or in a combination of two or more.

These catalysts may be supported by a carrier. The carrier is not particularly limited, and examples of carriers include porous alumina silicate (e.g., zeolite as a typical example), aluminum oxide, silicon oxide, activated carbon, titanium oxide, zirconia oxide, zinc oxide, and aluminum fluoride. These carriers can be used singly or in a combination of two or more, or as a structural composite of two or more. Specific examples of catalysts supported by a carrier include Cr2O3/Al2O3, Cr2O3/AlF3, Cr2O3/C, CoCl2/Cr2O3/Al2O3, NiCl2/Cr2O3/Al2O3, COCl2/AlF3, and NiCl2/AlF3.

Of these, preferable catalysts are chromium oxides, fluorinated chromium oxides, etc. Usable chromium oxide catalysts and fluorinated chromium oxides include crystalline chromium oxides and amorphous chromium oxides. More specifically, for example, at least one catalyst selected from the group consisting of chromium oxides and fluorinated chromium oxides, i.e., at least one catalyst selected from the group consisting of chromium oxides represented by composition formula: $CrO_m$ (1.5<m<3) and fluorinated chromium oxides obtained by fluorinating the chromium oxides, can suitably be used.

The reaction pressure in the dehydrohalogenation step is not particularly limited, and the reaction can be performed under reduced pressure, ordinary pressure, or increased pressure, with the reaction under ordinary pressure being preferable.

The reaction temperature in the dehydrohalogenation step can be 200 to 600° C. under ordinary pressure, with 250 to 450° C. being preferable.

The contact time in the dehydrohalogenation step may be typically about 0.1 to 300 g·sec/cc, and preferably 0.5 to 60 g·sec/cc. The contact time is represented by the ratio $W/F_0$: W indicates the catalyst amount (g) and $F_0$ indicates the total flow rate of gas supplied to the reactor in the dehydrohalogenation step (a flow rate at 0° C. at 1 atm:cc/sec).

The contact time in the dehydrohalogenation step where a catalyst is not used may be typically about 1 to 500 sec, which is a residence time indicated by the ratio $V/F_0$: V indicates the reaction space V (cc) in a gas phase, and $F_0$ indicates the total flow rate $F_0$ of gas supplied to the reactor (a flow rate at 0° C. at 0.1 MPa:cc/sec).

In the dehydrohalogenation step, oxygen gas may also be present during the reaction. If this is the case, the flow rate of oxygen gas (mol/min) is, for example, 0.1% or more and 30% or less, preferably 0.5% or more and 15% or less, and more preferably 1% or more and 10% or less, relative to the flow rate (mol/min) of fluorine-containing compound-containing composition A. This more likely inhibits the decrease in catalytic activity, and continuously gives the target fluorine-containing compound-containing composition B for an extended period of time at high selectivity.

In the hydrogenation step, fluorine-containing compound-containing composition A and hydrogen can be supplied to the reactor in the presence or absence of a reduction catalyst. The reduction catalyst is not particularly limited, and a typical reduction catalyst can be used. The reduction catalyst is also suitably selected depending on the embodiment. Of reduction catalysts, metals, such as Pd, Pt, Rh, Ru, and Rc, supported by activated carbon, metal oxides, such as alumina, or metal fluorides are preferable.

The reaction pressure in the hydrogenation step is not particularly limited, and the reaction can be performed under reduced pressure, ordinary pressure, or increased pressure, with the reaction under ordinary pressure or increased pressure being preferable.

The reaction temperature in the hydrogenation step is not particularly limited, and the reaction can be performed typically at 30 to 400° C. Within this range, 30 to 300° C. is preferable, and 30 to 180° C. is more preferable.

The contact time in the hydrogenation step where a catalyst is used may be typically about 0.5 to 30 g·sec/cc, and preferably 0.5 to 15 g·sec/cc. The contact time is represented by the ratio $W/F_0$: W indicates the catalyst amount (g) and $F_0$ indicates the total flow rate of gas supplied to the reactor in the hydrogenation step (a flow rate at 0° C. at 1 atm:cc/sec). The contact time can be suitably selected depending on the purpose, because the contact time affects the selectivity of the target fluorine-containing compound and the conversion of starting material compounds.

The contact time in the hydrogenation step where a catalyst is not used may be typically about 1 to 500 sec, which is a residence time indicated by the ratio $V/F_0$: V indicates the reaction space V (cc) in a gas phase, and $F_0$ indicates the total flow rate of gas supplied to the reactor (a flow rate at 0° C. at 0.1 MPa:cc/sec).

The hydrogen and fluorine-containing compound-containing composition A supplied to the reactor in the hydrogenation step are typically mixed at a ratio of their stoichiometric amounts or more and supplied to the reactor. Thus, the molar ratio of hydrogen/fluorine-containing compound-containing composition A for supply is typically within the range of 1 to 6, and preferably 1 to 3.

The fluorination step can be performed in the presence or absence of a fluorination catalyst. A known catalyst that shows activity in fluorination with hydrogen fluoride can be used as a fluorination catalyst. Examples of usable fluorination catalysts include metal oxides and fluorinated metal oxides, such as chromium oxide, fluorinated chromium oxide, aluminum fluoride, and fluorinated aluminum oxide. In addition, metal fluorides, such as $MgF_2$, $TaF_5$, and $SbF_5$ can also be used.

Of these catalysts, although there is no particular limitation, for example, a chromium oxide represented, for example, by composition formula: $CrO_m$ wherein $1.5<m<3$ is preferable, a chromium oxide represented by composition formula: $CrO_m$ wherein $2<m<2.75$ is more preferable, and a chromium oxide represented by composition formula: $CrO_m$ wherein $2<m<2.3$ is still more preferable. The chromium oxide catalyst for use can be of any shape, for example, powder or pellets, as long as it suits the reaction. In particular, pellets are preferable.

The reaction pressure in the fluorination step is not particularly limited, and the reaction can be performed under reduced pressure, ordinary pressure, or increased pressure, with the reaction under ordinary pressure or increased pressure being preferable.

The reaction temperature in the fluorination step under ordinary pressure can be 200 to 600° C., preferably 250 to 450° C., and more preferably 300 to 400° C.

The contact time in the fluorination step may be typically about 0.5 to 70 g·sec/cc and preferably 1 to 50 g·sec/cc. The contact time is represented by the ratio $W/F_0$: W indicates the catalyst amount (g) and $F_0$ indicates the total flow rate of gas supplied to the reactor in the hydrogenation step (a flow rate at 0° C. at 1 atm:cc/sec).

The contact time in the fluorination step where a catalyst is not used may typically be about 1 to 500 sec, which is a residence time indicated by the ratio $V/F_0$: V indicates the reaction space V (cc) in a gas phase, and $F_0$ indicates the total flow rate of gas supplied to the reactor (a flow rate at 0° C. at 0.1 MPa:cc/sec).

By-products that can be generated in this embodiment and that may have a low boiling point or a high boiling point can be suitably removed, for example, by distillation. Hydrogen fluoride generated during the steps can be suitably separated and removed by washing with water and/or distillation. The unreacted starting material compounds, intermediates, and like components can be supplied again to at least one step selected from the group consisting of the hydrogenation step, defluorination step, and hydrofluorination step.

Composition Supplied to Dehydrohalogenation Step

The production method of the present invention can supply at least part of fluorine-containing compound-containing composition A to the dehydrohalogenation step, composition A containing a mixture that contains at least one fluoroolefin represented by formula (1):

$$C_nF_mX_l \qquad (1)$$

wherein n, m, and l represent an integer of 1 or more, $m+l=2n$, $n\geq 2$, Xs each independently represent one atom selected from the group consisting of halogens and hydrogen, at least one hydrofluorocarbon represented by formula (2):

$$C_pF_qY_rH_s \qquad (2)$$

wherein p, q, r, and s represent an integer of 1 or more, $q+r+s=2p+2$, Ys each independently represent one atom selected from the group consisting of halogens and hydrogen, the difference in boiling point between the at least one fluoroolefin and the at least one hydrofluorocarbon being less than 9° C., or the at least one fluoroolefin and the at least one hydrofluorocarbon forming an azeotropic mixture or a pseudo-azeotropic mixture. The difference in the boiling points is preferably less than 9° C., preferably less than 7° C., and more preferably less than 5° C.

The halogen atoms present in the fluoroolefin represented by formula (1) and the hydrofluorocarbon represented by formula (2) are preferably fluorine.

Because the hydrofluorocarbon represented by formula (2) contains only saturated bonds, hydrogen and halogen atoms bound to a carbon that forms saturated bonds are preferentially detached in the dehydrohalogenation step, thereby forming unsaturated bonds.

The likelihood of the reaction that replaces a halogen atom with a hydrogen atom is indicated by F<Cl<Br<I. Thus, in an embodiment of the present invention, particularly where the hydrogenation step is included, the effect of the present invention becomes more prominent, if the halogen atoms present in the fluoroolefin represented by formula (1) and the hydrofluorocarbon represented by formula (2) are all fluorine. However, this does not exclude the case where I, Br, and Cl are present in these compounds. When these halogen atoms are present, the reaction conditions can suitably be changed, for example, by adjusting the reaction temperature in the hydrogenation step to 200° C. or less, and more preferably 100° C. or less. However, the reaction temperature in the hydrogenation step is not limited to the temperature within the ranges.

The fluoroolefin represented by formula (1) is not particularly limited, and examples of the fluoroolefin include 1225ye, 1234ze, 1225zc, 1243zf, HFO-1132, 1234yf, HFP, HFO-1123, HFO-1141, HFO-1114, and 1132a.

The hydrofluorocarbon represented by formula (2) is not particularly limited, and examples of the hydrofluorocarbon include 245cb, 236fa, 227ea, HFC-134, HFC-152a, 134a, HFC-161, 143a, and HFC-125.

A combination of the fluoroolefin represented by formula (1) and the hydrofluorocarbon represented by formula (2) provides the effect of the present invention more remarkably, when the difference in their boiling points is less than 9° C.

Specifically, when the difference in boiling point between the fluoroolefin represented by formula (1) and the hydrofluorocarbon represented by formula (2) is as small as, for example, less than 9° C., the separation of these compounds typically requires a cumbersome separation technique, such as a rectification column involving many stages and extractive distillation. However, supplying these compounds together to the dehydrohalogenation step makes it possible to dehydrohalogenate only the hydrofluorocarbon represented by formula (2) to thereby obtain a mixture of compounds, the boiling points of which are not close to each other. Separating and recovering a necessary compound from such a mixture using the difference in the boiling points does not require a cumbersome separation technique and equipment mentioned above, and thus provides the target compound in an advantageous way from the standpoint of equipment and operation costs.

The combination of the fluoroolefin represented by formula (1) and the hydrofluorocarbon represented by formula (2) is preferably a mixture of these compounds, the boiling points of which are different by less than 9° C., an azeotropic mixture formed by these compounds, or a pseudo-azeotropic mixture formed by these compounds. More specifically, for example, the combinations shown in Table 2 below are preferable.

TABLE 2

| Combination | Formula (1) | Formula (2) |
| --- | --- | --- |
| 1 | 1234ze | 245cb, 227ea, HFC-134, 152a, and/or 134a |
| 2 | 1234yf | 245cb, HFC-134, 152a, 134a, and/or HFC-161 |
| 3 | 1225ye | 245cb, HFC-134, 152a, and/or 134a |
| 4 | HFP | HFC-134, 152a, 134a, and/or HFC-161 |
| 5 | 1225zc | 245cb, 227ea, HFC-134, 152a, and/or 134a |
| 6 | 1243zf | 245cb, 227ea, HFC-134, 152a, and/or 134a |
| 7 | HFO-1132 | 245cb, 227ea, HFC-134, 152a, and/or 134a |
| 8 | HFO-1123 | 143a and/or HFC-125 |

Fluorine-containing compound-containing composition A may consist of only a mixture in any of the combinations shown above or may also contain other compounds in addition to the mixture, and preferably contains the starting material compound of the target fluorine-containing compound and/or the intermediates.

The content of the fluoroolefin represented by formula (1) and the content of the fluorocarbon represented by formula (2) in fluorine-containing compound-containing composition A are not particularly limited. The content, indicated by a mole fraction, of at least one member selected from the group consisting of the fluoroolefin represented by formula (1) and the fluorocarbon represented by formula (2) contained in fluorine-containing compound-containing composition A is preferably about 0.1 mol % or more, more preferably 1 mol % or more, and still more preferably 5 mol % or more of fluorine-containing compound-containing composition A.

The molar ratio of the fluoroolefin represented by formula (1) to the fluorocarbon represented by formula (2) contained in fluorine-containing compound-containing composition A (the fluoroolefin represented by formula (1): the fluorocarbon represented by formula (2)) is not particularly limited, and is preferably within the range of 0.1:99.9 to 99.1:0.1, and more preferably within the range of 5:95 to 95:5. Additionally, to make the effect of the present invention more prominent, the molar ratio is preferably within the range of 10:90 to 90:10, and more preferably within the range of 30:70 to 70:30.

Composition Obtained in Step D

Because of step D, it is possible to obtain fluorine-containing compound-containing composition B that contains a mixture that contains at least one fluoroolefin represented by formula (1) and at least one fluoroolefin represented by formula (3)

It is sufficient if the at least one fluoroolefin represented by formula (3) has a boiling point or boiling points different from that or those of the at least one fluoroolefin represented by formula (1) by 9° C. or more, or does not form an azeotropic mixture or a pseudo-azeotropic mixture together with the at least one fluoroolefin represented by formula (1). More specifically, the at least one fluoroolefin represented by formula (3) is not particularly limited, as long as it can be obtained by dehydrohalogenation of the hydrofluorocarbon represented by formula (2), and examples include 1225zc, HFP, HFO-1123, HFO-1141, HFO-1114, 1132a, and 1234yf. Of these, 1234yf is preferable.

More specifically, preferable examples of the combination of the fluoroolefin represented by formula (1) and the fluoroolefin represented by formula (3) include those shown in Table 3 below.

TABLE 3

| Combination | Formula (1) | Formula (3) |
|---|---|---|
| 1 | 1234ze | HFP, HFO-1123, HFO-1141, HFO-1114, 1132a and/or 1234yf |
| 2 | 1234yf | HFO-1123, HFO-1141, HFO-1114 and/or 1132a |
| 3 | 1225ye | HFP, HFO-1123, HFO-1141, HFO-1114, 1132a and/or 1234yf |
| 4 | HFP | HFO-1123, HFO-1141, HFO-1114 and/or 1132a |
| 5 | 1225zc | HFO-1123, HFO-1141, HFO-1114 and/or 1132a |
| 6 | 1243zf | HFO-1123, HFO-1141, HFO-1114 and/or 1132a |
| 7 | HFO-1132 | 1225zc, HFP, HFO-1123, HFO-1141, HFO-1114, 1132a and/or 1234yf |
| 8 | HFO-1123 | 1225zc, HFP, HFO-1123, HFO-1141, HFO-1114, 1132a and/or 1234yf |

Fluorine-containing compound-containing composition B may consist of only a mixture in any of the combinations above or may also contain other compounds in addition to the mixture, but preferably contains the starting material compound of the target fluorine-containing compound and/or the intermediates.

In an embodiment of the present invention, step D subjects the hydrofluorocarbon represented by formula (2) to dehydrohalogenation to convert the hydrofluorocarbon represented by formula (2) into at least one fluoroolefin represented by formula (3): $C_pF_qZ_t$ wherein p, q, and t represent an integer of 1 or more, p≥2, q+t=2p, and Zs each independently represent one atom selected from the group consisting of halogens and hydrogen.

This provides easily purifiable fluorine-containing compound-containing composition B that contains a mixture that contains the at least one fluoroolefin represented by formula (1) and the at least one fluoroolefin represented by formula (3), the boiling points of which are different by 9° C. or more.

In another embodiment of the present invention, step D provides easily purifiable fluorine-containing compound-containing composition B that contains a mixture that contains the at least one fluoroolefin represented by formula (1) and the at least one fluoroolefin represented by formula (3) wherein the at least one fluoroolefin represented by formula (1) and the at least one fluoroolefin represented by formula (3) do not foam an azeotropic mixture or a pseudo-azeotropic mixture.

Method 1 for Producing Fluorine-Containing Compound that Comprises Step D

An embodiment of the method for producing a fluorine-containing compound according to the present invention is a method for producing 1234yf from 1225ye. The following is an outline of the steps of producing 1234yf from 1225ye as a starting material.

Specifically, at least 1225ye is supplied to the first hydrogenation step to obtain mixture product 1 containing at least 245eb, and mixture product 1 containing at least 245eb is supplied to the first dehydrohalogenation step to obtain mixture product 2 containing at least 1234yf.

In this stage, mixture product 2 containing at least 1234yf may contain 1234ze represented by formula (1) and 245cb represented by formula (2) as by-products in addition to 1234yf.

245cb generated as a by-product can be converted into 1234yf by dehydrohalogenation, but the same does not apply to 1234ze. To reduce further generation of by-products, it is typically preferable to recover only 245cb and supply 245cb to the dehydrohalogenation step.

However, 1234ze(E) and 245cb have very close boiling points (−19° C. and −18° C. respectively), which makes it difficult to extract only 245cb from fluorine-containing compound-containing composition A that contains a mixture of these by-products, and to subject 245cb to dehydrohalogenation.

The production method of the present invention, however, can convert 245cb into 1234yf represented by formula (3) owing to step D where fluorine-containing compound-containing composition A that contains a mixture of these by-products is supplied to the dehydrohalogenation step, thereby providing fluorine-containing compound-containing composition B that contains a mixture that contains 1234ze and 1234yf.

In this stage, supplying composition B to the separation step of recovering 1234yf from mixture product 2 containing, together with 1234yf, 1234ze and 245cb as by-products (i.e., mixture product 2 containing at least 1234yf) provides fluorine-containing compound-containing composition A. The separation step can be performed using the difference in the boiling points of these compounds with a known technique.

As noted above, it is difficult to extract only 245cb from fluorine-containing compound-containing composition A that contains a mixture of 1234ze and 245cb and subject it to dehydrohalogenation to obtain 1234yf. However, due to the boiling point of 1234yf being −28° C., which has a sufficiently wide gap from the boiling point of 1234ze, it becomes easy to recover only 1234yf from fluorine-containing compound-containing composition B using the difference in boiling point in the separation step. The separation step of separating 1234yf from fluorine-containing compound-containing composition B to recover 1234yf can be performed using the difference in the boiling points of these compounds with a known technique.

Additionally, the presence of 1234ze in fluorine-containing compound-containing composition B reduces the generation of 1234ze as an additional by-product in the dehydrohalogenation step. This effect is inferred from the principle of chemical equilibrium.

Step D may supply fluorine-containing compound-containing composition B to the first dehydrohalogenation step, or to a dehydrohalogenation step other than the first dehydrohalogenation step. To reduce the equipment and operation costs for the entire method for producing a fluorine-containing compound, it is preferable to circulate fluorine-containing compound-containing composition B and supply composition B together with mixture product 1 containing at least 245eb to the first dehydrohalogenation step.

If fluorine-containing compound-containing composition B is supplied to a dehydrohalogenation step other than the first dehydrohalogenation step, the reaction temperature in the dehydrohalogenation step is preferably higher than the reaction temperature in the first dehydrohalogenation step.

Method 2 for Producing Fluorine-Containing Compound that Comprises Step D

An embodiment of the method for producing a fluorine-containing compound according to the present invention is a method for producing 1234yf from HFP. The following is an outline of the steps of producing 1234yf from HFP as a starting material.

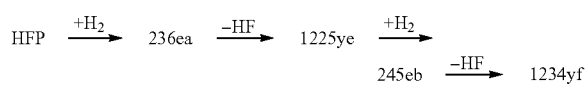

Specifically, at least HFP is supplied to the first hydrogenation step to obtain mixture product 1 containing at least 236ea, and mixture product 1 is supplied to the first dehydrohalogenation step to obtain mixture product 2 containing at least 1225ye. Mixture product 2 is supplied to the second hydrogenation step to obtain mixture product 3 containing at least 245eb, and mixture product 3 is supplied to the second dehydrohalogenation step to obtain mixture product 4 containing at least 1234yf.

In this stage, mixture product 4 may contain 1234ze represented by formula (1) and 245cb represented by formula (2) as by-products in addition to 1234yf.

The production method of the present invention can convert 245cb into 1234yf represented by formula (3) owing to step D where fluorine-containing compound-containing composition A that contains a mixture of these by-products is supplied to the dehydrohalogenation step, thereby providing fluorine-containing compound-containing composition B that contains a mixture that contains 1234ze and 1234yf.

In this stage, supplying composition B to the separation step of recovering only 1234yf from the mixture product containing 1234ze and 245cb as by-products together with 1234yf (i.e., a mixture product containing at least 1234yf) provides fluorine-containing compound-containing composition A. The separation step can be performed using the difference in the boiling points of these compounds with a known technique.

In this stage, it becomes easy to extract and recover only 1234yf from fluorine-containing compound-containing composition B using the difference in boiling point, as described above. The separation step of separating 1234yf from fluorine-containing compound-containing composition B to recover 1234yf can be performed using the difference in the boiling points of these compounds with a known technique.

Step D may supply fluorine-containing compound-containing composition B to either dehydrohalogenation step 1 or 2 or both, and may also supply composition B to a hydrogenation step other than dehydrohalogenation steps 1 and 2. To reduce the equipment and operation costs for the entire method for producing a fluorine-containing compound, it is preferable to circulate fluorine-containing compound-containing composition B and supply composition B together with mixture product 1 or 2 to either the first or second dehydrohalogenation step or both.

As described above, the presence of 1234ze in fluorine-containing compound-containing composition B reduces the generation of 1234ze as an additional by-product in the dehydrohalogenation step.

The production method of the present invention can further comprise the step of supplying mixture product 2 that further contains 1234ze to the second hydrogenation step to convert 1234ze into 254fb.

The reaction temperature in at least one of the dehydrohalogenation steps, which provides fluorine-containing compound-containing composition B, is preferably higher than the reaction temperature in the second dehydrohalogenation step.

The method described above enables efficient recovery of a by-product useful as an intermediate of the target product using a wide difference between boiling points. Additionally, this can reduce the equipment and operation costs required for separating the by-product; i.e., an economically advantageous method for producing a fluorine-containing compound is provided.

EXAMPLES

The following Examples describe the present invention in more detail.

Example 1

Anhydrous hydrogen fluoride diluted with nitrogen was passed through a reactor that contained, as a catalyst, chromium oxide containing $CrO_m$ ($2 \leq m < 3$) as a major component, and the temperature of the reactor was set to 200° C. to 380° C. to fluorinate the chromium oxide. After the reactor was heated to a predetermined temperature, a mixture gas containing 1234ze and 245cb at a molar ratio of 1:1 (1234ze:245cb) and oxygen were supplied to the reactor, and the supply of nitrogen was halted. Oxygen was introduced from the reactor inlet so that the amount of oxygen became 5 mol % relative to 245cb at the reactor inlet. The reaction pressure was 0.0 MPaG, and the reaction temperature was 200 to 380° C., with the contact time (W/$F_0$) being 5 g·sec/cc. The component composition at the reactor outlet was analyzed by gas chromatography. Table 4 shows the results.

TABLE 4

| Run No. | Reaction Temperature (° C.) | Composition at the Outlet (%) | | | | | | | | |
|---|---|---|---|---|---|---|---|---|---|---|
| | | 1234yf | 245cb | 1234ze | 1225ye | 236ea | 1243zf | CF3C≡CH | 143a | CO2 | Others |
| 1 | 350 | 23.6 | 21.1 | 50.1 | 0.0 | 0.0 | 0.1 | 0.0 | 0.0 | 5.1 | 0.0 |
| 2 | 380 | 25.6 | 12.7 | 50.1 | 0.0 | 0.0 | 0.1 | 0.0 | 0.0 | 11.5 | 0.0 |

Example 2

Anhydrous hydrogen fluoride diluted with nitrogen was passed through a reactor that contained, as a catalyst, chromium oxide containing $CrO_m$ ($2 \leq m < 3$) as a major component, and the temperature of the reactor was set to 200° C. to 380° C. to fluorinate the chromium oxide. After the reactor was heated to a predetermined temperature, a mixture gas containing 1234ze, 236ea, and 245cb at a molar ratio of 2:1:1 (1234ze:236ea:245cb) and oxygen were supplied to the reactor, and the supply of nitrogen was halted. Oxygen was introduced from the reactor inlet so that the amount of oxygen became 5 mol % relative to the total amount of 245cb and 236ea at the reactor inlet. The reaction pressure was 0.0 MPaG, and the reaction temperature was 200 to 380° C., with the contact time (W/$F_0$) being 5 g·sec/cc. The component composition at the reactor outlet was analyzed by gas chromatography. Table 5 shows the results.

TABLE 5

| Run No. | Reaction Temperature (° C.) | Composition at the Outlet (%) | | | | | | | | |
|---|---|---|---|---|---|---|---|---|---|---|
| | | 1234yf | 245cb | 1234ze | 1225ye | 236ea | 1243zf | CF3C≡CH | 143a | CO2 | Others |
| 1 | 350 | 11.8 | 10.6 | 50.1 | 19.4 | 4.7 | 0.1 | 0.0 | 0.1 | 3.1 | 0.3 |
| 2 | 380 | 12.8 | 6.4 | 50.0 | 13.4 | 10.8 | 0.1 | 0.0 | 0.0 | 6.1 | 0.3 |

Comparative Example 1

An attempt was made to separate a mixture gas containing 1234ze(E) and 245cb at a molar ratio of about 4:1 (1234ze(E):245cb) by rectification under increased pressure using a rectification column. Table 6 shows the results of analysis of the composition of gas recovered from the column top.

TABLE 6

| Fraction No. | 1234ze (E) | 245cb | Other Low-boiling Components |
|---|---|---|---|
| 1 | 0.1 | 0.0 | >99 |
| 2 | 1.8 | 0.5 | >97 |

In Fraction No. 1, components having lower boiling points than 1234ze(E) were obtained from the column top with a purity of 99% or more by rectification of the mixture gas containing 1234ze(E) and HFC-245cb. As the extraction of low-boiling components proceeded, the amount of the low-boiling components in the rectification column decreased. This, in turn, increased the concentration of high-boiling components and initiated the distillation of 1234ze(E), which was the second low-boiling component, from the column top. Fraction No. 2 was obtained when 1234ze(E) was present in an amount of more than 1 mol % of the entire components, and distillation of 1234ze(E) had already begun to increase. At that stage, the second high-boiling component, 245cb, was already mixed at a molar ratio of about 4:1 (1234ze(E):HFC-245cb).

Specifically, when the distillation of 1234ze(E) started, a considerable amount of HFC-245cb was already mixed. This indicates that separation of these components was difficult.

The invention claimed is:

1. A method for producing a fluorine-containing compound, the method comprising step D of supplying at least part of fluorine-containing compound-containing composition A to a dehydrohalogenation step, composition A containing a mixture that contains at least one fluoroolefin represented by formula (1):

$$C_nF_mX_l \qquad (1)$$

wherein n, m, and l represent an integer of 1 or more, m+l=2n, n≥2, and Xs each independently represent one atom selected from the group consisting of halogens and hydrogen, and at least one hydrofluorocarbon represented by formula (2):

$$C_pF_qY_rH_s \qquad (2)$$

wherein p, q, r, and s represent an integer of 1 or more, q+r+s=2p+2, and Ys each independently represent one atom selected from the group consisting of halogens and hydrogen with at least one of Ys being a halogen atom, the difference in boiling point between the at least one fluoroolefin and the at least one hydrofluorocarbon being less than 9° C., or the at least one fluoroolefin and the at least one hydrofluorocarbon forming an azeotropic mixture or a pseudo-azeotropic mixture.

2. The production method according to claim 1 wherein the fluoroolefin represented by formula (1) is at least one halogenated fluoroolefin selected from the group consisting of 1,1,1,2,3-pentafluoropropene (HFO-1225ye), 1,1,1,3-tetrafluoropropene (HFO-1234ze), 1,1,1,3,3-pentafluoropropene (HFO-1225zc), 1,1,1-trifluoropropene (HFO-1243zf), 1,2-difluoroethylene (HFO-1132), 2,3,3,3-tetrafluoropropene (HFO-1234yf), hexafluoropropene (HFP), trifluoroethylene (HFO-1123), fluoroethylene (HFO-1141), tetrafluoroethylene (HFO-1114), and 1,1-difluoroethylene (HFO-1132a); and the hydrofluorocarbon represented by formula (2) is at least one saturated halogenated fluorocarbon selected from the group consisting of 1,1,1,2,2-pentafluoropropane (HFC-245 cb), 1,1,1,3,3,3-hexafluoropropane (HFC-236fa), 1,1,1,2,3,3,3-heptafluoropropane (HFC-227ea), 1,1,2,2-hexafluoroethane (HFC-134), 1,1-difluoroethane (HFC-152a), 1,1,1,2-hexafluoroethane (HFC-134a), fluoroethane (HFC-161), 1,1,1-trifluoroethane (HFC-143a), and 1,1,1,2,2-pentafluoroethane (HFC-125).

3. The production method according to claim 1 wherein in step D the at least one hydrofluorocarbon represented by formula (2) is converted into at least one fluoroolefin represented by formula (3):

$$C_pF_qZ_t \qquad (3)$$

wherein p, q, and t represent an integer of 1 or more, p≥2, q+t=2p, and Zs each independently represent one atom selected from the group consisting of halogens and hydrogen to obtain fluorine-containing compound-containing composition B that contains a mixture that contains the at least one fluoroolefin represented by formula (1) and the at least one fluoroolefin represented by formula (3), the at least one fluoroolefin represented by formula (3) having a boiling point or boiling points that differ by 9° C. or more from that of the fluoroolefin represented by formula (1).

4. The production method according to claim 3 further comprising the step of separating at least part of fluorine-containing compound-containing composition B that contains a mixture that contains the at least one fluoroolefin represented by formula (1) and the at least one fluoroolefin represented by formula (3) into a fraction rich in the at least one fluoroolefin represented by formula (3) and a fraction containing a reduced amount of the at least one fluoroolefin represented by formula (3).

5. The production method according to claim 3 wherein the at least one fluoroolefin represented by formula (3) is at least one saturated halogenated fluorocarbon selected from the group consisting of 1,1,1,3,3-pentafluoropropene (HFO-1225zc), hexafluoropropene (HFP), trifluoroethylene (HFO-1123), fluoroethylene (HFO-1141), tetrafluoroethylene (HFO-1114), 1,1-difluoroethylene (HFO-1132a), and 2,3,3,3-tetrafluoropropene (HFO-1234yf).

6. The production method according to claim 1 further comprising either a hydrogenation step or a fluorination step, or both of the steps.

7. The production method according to claim 4 wherein the separation step comprises at least one member selected from the group consisting of distillation, extractive distillation, liquid-liquid separation, and membrane separation.

8. The production method according to claim 1 wherein the fluorine-containing compound is at least one fluorine-containing compound selected from the group consisting of fluorine-containing compounds represented by formula (4):

$$CF_3CX=CYZ \quad (4)$$

wherein X, Y, and Z each independently represent a fluorine atom or a hydrogen atom.

9. The production method according to claim 8 wherein the fluorine-containing compounds represented by formula (4) are at least one fluorine-containing compound selected from the group consisting of 1,1,1,3-tetrafluoropropene (HFO-1234ze) and 2,3,3,3-tetrafluoropropene(HFO-1234yf).

10. The production method according to claim 1 wherein a starting material compound for producing the fluorine-containing compound contains at least one member selected from the group consisting of hexafluoropropene (HFP), 1,1,1,2,3-pentafluoropropene (HFO-1225ye), and 3-chloro-1,1,1,2,2-pentafluoropropane (HCFC-235cb).

11. The production method according to claim 10 wherein the fluorine-containing compounds represented by formula (4) are at least one fluorine-containing compound selected from the group consisting of 1,1,1,3-tetrafluoropropene (HFO-1234ze) and 2,3,3,3-tetrafluoropropene (HFO-1234yf), the starting material compound is at least one fluorine-containing compound selected from the group consisting of hexafluoropropene (HFP), 1,1,1,2,3-pentafluoropropene (HFO-1225ye), and 3-chloro-1,1,1,2,2-pentafluoropropane (HCFC-235 cb), the at least one fluoroolefin represented by formula (1) is 1,1,1,3-tetrafluoropropene (HFO-1234ze), the at least one hydrofluorocarbon represented by formula (2) is 1,1,1,2,2-pentafluoropropane (HFC-245cb), and the at least one fluoroolefin represented by formula (3) is 2,3,3,3-tetrafluoropropene (HFO-1234yf).

12. The production method according to claim 6 wherein at least one of the hydrogenation steps is a gas-phase reaction.

13. The production method according to claim 6 wherein at least one of the hydrogenation steps is a liquid-phase reaction.

14. The production method according to claim 6 wherein at least one of the fluorination steps is a gas-phase reaction.

15. The production method according to claim 6 wherein at least one of the fluorination steps is a liquid-phase reaction.

16. A method for producing 2,3,3,3-tetrafluoropropene (HFO-1234yf), the method comprising the steps of
1) supplying at least 1,1,1,2,3-pentafluoropropene (HFO-1225ye) to a first hydrogenation step to obtain mixture product 1 containing 1,1,1,2,3-pentafluoropropane (HFC-245eb),
2) supplying mixture product 1 to a first dehydrohalogenation step to obtain mixture product 2 containing 2,3,3,3-tetrafluoropropene (HFO-1234yf) and 1,1,1,2,2-pentafluoropropane (HFC-245 cb),
3) supplying mixture product 2 to a separation step to separate mixture product 2 into a mixture containing HFO-1234yf and a mixture containing HFO-1234ze and HFC-245cb, and
4) supplying the mixture containing HFO-1234ze and HFC-245cb to either the first dehydrohalogenation step or a dehydrohalogenation step other than the first dehydrohalogenation step, or both of the steps to dehydrohalogenate HFC-245cb, thereby converting HFC-245cb into HFO-1234yf.

17. The production method according to claim 16 wherein the mixture containing HFO-1234ze and HFC-245cb is supplied to a dehydrohalogenation step other than the first dehydrohalogenation step.

18. The production method according to claim 16 wherein a reaction temperature in the dehydrohalogenation step other than the first dehydrohalogenation step is higher than a reaction temperature in the first dehydrohalogenation step.

19. The production method according to claim 16 comprising a separation step of recovering HFO-1234yf from the mixture obtained by subjecting the mixture containing HFO-1234ze and HFC-245cb to dehydrohalogenation.

20. A method for producing 2,3,3,3-tetrafluoropropene (HFO-1234yf), the method comprising the steps of
1) supplying at least hexafluoropropene (HFP) to a first hydrogenation step to obtain mixture product 1 containing 1,1,1,2,3,3-hexafluoropropane (HFC-236ea),
2) supplying mixture product 1 to a first dehydrohalogenation step to obtain mixture product 2 containing 1,1,1,2,3-pentafluoropropene (HFO-1225ye),
3) supplying mixture product 2 to a second hydrogenation step to obtain mixture product 3 containing HFC-245eb,
4) supplying mixture product 3 to a second dehydrohalogenation step to obtain mixture product 4 containing HFO-1234ze, HFC-245cb, and HFO-1234yf, and
5) supplying mixture product 4 to a separation step to separate mixture product 4 into a mixture containing HFO-1234yf and a mixture containing HFO-1234ze and HFC-245cb, and
supplying the mixture containing HFO-1234ze and HFC-245cb to at least any one of
the first dehydrohalogenation step and the second dehydrofluorination step,
the first dehydrohalogenation step,
the second dehydrohalogenation step, or
a dehydrohalogenation step other than the first and second dehydrohalogenation steps
to dehydrohalogenate HFC-245cb, thereby converting HFC-245cb into HFO-1234yf.

21. The production method according to claim 20 wherein the mixture containing HFO-1234ze and HFC-245cb is supplied to the first dehydrohalogenation step.

22. The production method according to claim 20 wherein mixture product 2 further contains HFO-1234ze, and mixture product 2 is supplied to the second hydrogenation step to convert HFO-1234ze into HFC-254fb.

23. The production method according to claim 20 wherein a reaction temperature in at least one of the dehydrohalogenation steps to which the mixture containing HFO-1234ze and HFC-245cb is supplied is higher than a reaction temperature in the second dehydrohalogenation step.

24. The production method according to claim 20 comprising a separation step of recovering HFO-1234yf from the mixture obtained by subjecting the mixture containing HFO-1234ze and HFC-245cb to dehydrohalogenation.

* * * * *